(12) United States Patent
Victor

(10) Patent No.: US 9,101,370 B2
(45) Date of Patent: Aug. 11, 2015

(54) DISPOSABLE SURGICAL CUTTER FOR SHAPING THE HEAD OF A FEMUR

(75) Inventor: Gary C. Victor, Wheatfield, NY (US)

(73) Assignee: Greatbatch Ltd., Clarence, NY (US)

( * ) Notice: Subject to any disclaimer, the term of this patent is extended or adjusted under 35 U.S.C. 154(b) by 547 days.

(21) Appl. No.: 13/157,350

(22) Filed: Jun. 10, 2011

(65) Prior Publication Data

US 2011/0306980 A1     Dec. 15, 2011

Related U.S. Application Data

(60) Provisional application No. 61/353,699, filed on Jun. 11, 2010.

(51) Int. Cl.
*A61B 17/00* (2006.01)
*A61B 17/16* (2006.01)
*A61B 17/17* (2006.01)

(52) U.S. Cl.
CPC ........... *A61B 17/1668* (2013.01); *A61B 17/175* (2013.01)

(58) Field of Classification Search
CPC ........... A61B 17/1611; A61B 17/1668; A61B 17/175
USPC .................................. 606/79–84; 407/40, 47
See application file for complete search history.

(56) References Cited

U.S. PATENT DOCUMENTS

| | | | | | |
|---|---|---|---|---|---|
| 2,468,562 | A | * | 4/1949 | Lank | 144/219 |
| 2,618,991 | A | * | 11/1952 | Charles | 408/146 |
| 2,803,153 | A | * | 8/1957 | Golbeck | 408/174 |
| 3,257,871 | A | * | 6/1966 | Goodyear | 408/218 |
| 5,100,267 | A | | 3/1992 | Salyer | |
| 5,299,893 | A | | 4/1994 | Salyer et al. | |
| 5,549,704 | A | * | 8/1996 | Sutter | 623/23.13 |
| 7,097,397 | B2 | * | 8/2006 | Keightley | 408/204 |
| 2003/0212401 | A1 | | 11/2003 | Nordman | |
| 2004/0193168 | A1 | * | 9/2004 | Long et al. | 606/80 |
| 2005/0251145 | A1 | * | 11/2005 | Desarzens et al. | 606/80 |
| 2006/0111725 | A1 | | 5/2006 | Biegun | |
| 2007/0299451 | A1 | * | 12/2007 | Tulkis | 606/79 |
| 2009/0326536 | A1 | | 12/2009 | Pynsent | |

FOREIGN PATENT DOCUMENTS

| | | |
|---|---|---|
| EP | 0574701 | 5/1993 |
| WO | 2008001104 | 1/2008 |

* cited by examiner

*Primary Examiner* — David Bates
*Assistant Examiner* — Michael Araj
(74) *Attorney, Agent, or Firm* — Steven W. Winn; Michael F. Scalise

(57) ABSTRACT

A single use bone cutter comprised of a plate with a plurality of insert blade enclosures is described. The insert blade enclosures are arranged in a spiral pattern about the plate and are further positioned at varying height intervals through the thickness of the plate. The bone cutter provides a means whereby the insert blades can be easily positioned within the plurality of blade enclosures to provide a wide array of cutting diameters.

37 Claims, 10 Drawing Sheets

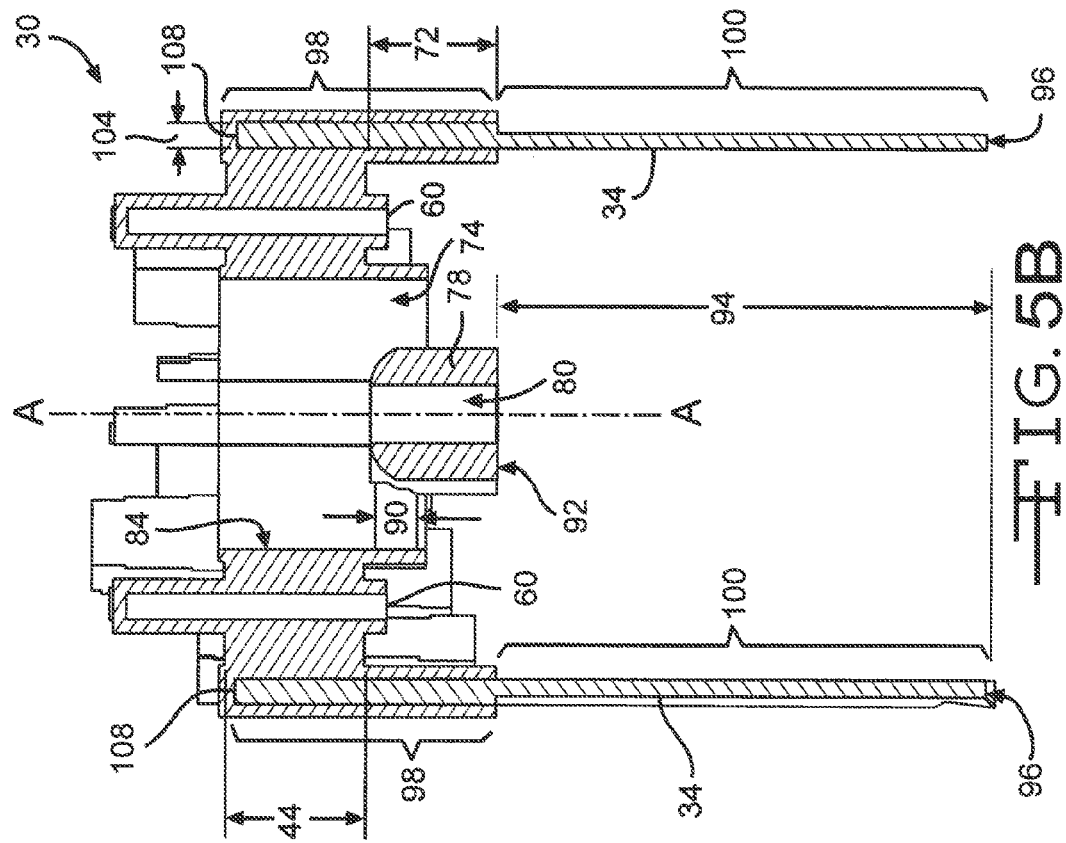
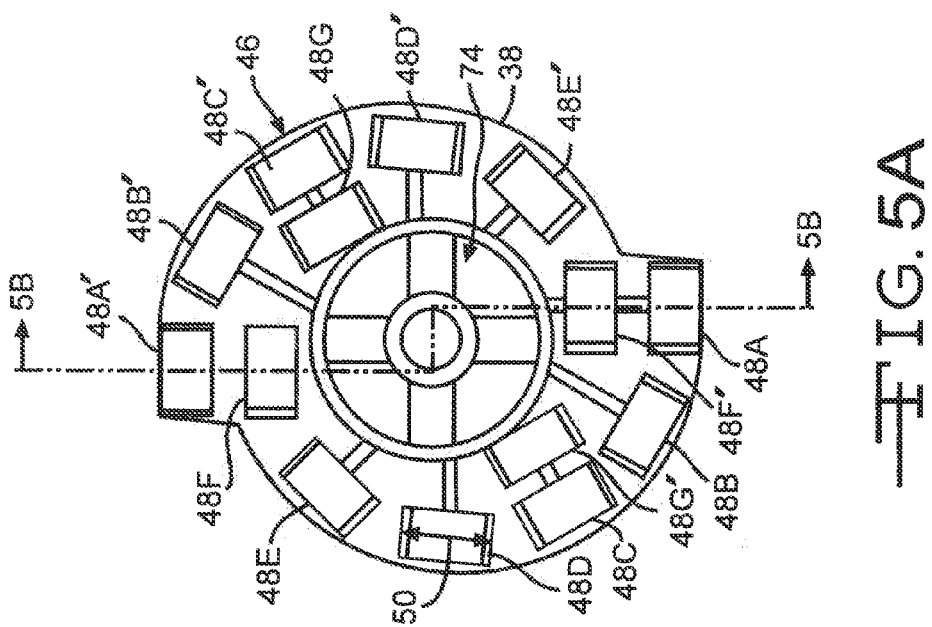

DISPOSABLE SURGICAL CUTTER FOR SHAPING THE HEAD OF A FEMUR

CROSS-REFERENCE TO RELATED APPLICATIONS

This application claims priority from U.S. Provisional Patent Application Ser. No. 61/353,699, filed Jun. 11, 2010.

FIELD OF THE INVENTION

The present invention, relates to the art of orthopedic cutting tools, and more particularly, to a disposable cutter used for shaping and preparing the femoral bone for implant insertion.

PRIOR ART

Cutting tools used in orthopedic procedures are designed to cut bone and associated tissue matter. Specifically, cutters of the present invention are designed to cut and shape the end of a long bone such as a femur or humerus. Typically, the end of the long bone is cut and shaped for insertion of an implant. As such, these cutters are required to be sterile and sharp. Using a dull cutter generates heat that typically leads to tissue necrosis and results in undesirable patient outcomes. A non-sterile cutter blade typically results in an infected and damaged bone that may lead to other problems for the patient.

Depicted in FIG. 1 is an image of a prior art bone cutter 10 designed to cut and shape the femoral head 12 of the femur 14. As shown in the figure, the prior art cutter 10 is similar to that of a "hole saw" drill. These prior devices 10 generally comprise a hollow cylinder in which a series of fixed cutting teeth slots 16 are formed within the cylinder wall thickness 18. Specifically, these prior art cutters 10 are designed with a fixed, predetermined diameter. As such, these prior art cutters 10 cannot be easily modified to accommodate a wide range of bone diameters.

In addition, traditional bone cutters are typically reused multiple times. That is because of their high cost. Such multiple reuses require that the cutter be cleaned and sterilized before each use. Furthermore, over time, as these cutters are used and reused, they become dull, thus requiring resharpening. Therefore the blades of the cutter are required to be resharpened, cleaned and sterilized. However, these resharpening and sterilization processes add additional costs and increase the possibility of infection. In addition, resharpening tends to deform the dimensions of the cutter. These dimensional changes could adversely impact the optimal fit and function of the implant. Furthermore, there is a high likelihood that the cleaning and sterilization process may not remove all possible infection agents such as bacteria, machining lubricants, and the like.

Accordingly, the present invention provides a cost effective single use bone cutter with a novel blade and assembly design. These design features provide for a bone cutter that is easily adaptable to cut and shape an array of bone diameters. In addition to ensuring proper cutter sharpness and cleanliness that promotes optimal patient outcomes, the enhanced bone cutting features of the present invention ensure proper implant fit and reduced implant wear.

SUMMARY OF THE INVENTION

The present invention provides a disposable bone cutter device comprising a cutter housing assembly, insert blades and guide-rod for orthopedic surgical applications. Specifically, the cutter device of the present invention is designed to re-shape the head of a femur for joint revision surgeries.

The cutter of the present invention is designed with a plurality of discreet insert blade enclosures within which an insert blade resides. These blade enclosures are further oriented in a "step wise" spiral formation which allows for the creation of customizable cutting diameters. Therefore, unlike the prior art, the bone cutter of the present invention allows for a cutting diameter that can be finely tuned to match the diameter of an implant.

In a preferred embodiment of the bone cutter of the present invention, the blade enclosures are positioned such that they are equidistant about a central longitudinal axis. This design aspect provides for precise concentric circular cutting of the bone.

The cutter housing assembly further comprises insert blades which can be easily inserted into their respective blade enclosures. Each insert blade comprises a blade cutting surface and a chamferred region which minimizes interference of the cut through the bone.

BRIEF DESCRIPTION OF THE DRAWINGS

FIG. 5A is a top view of the embodiment of the bone cutter shown in FIGS. 3 and 4.

FIG. 5B is a cross-sectional view of the bone cutter taken along cross-sectional line 5B-5B of FIG. 5A.

DETAILED DESCRIPTION OF THE PREFERRED EMBODIMENTS

Figure 1:
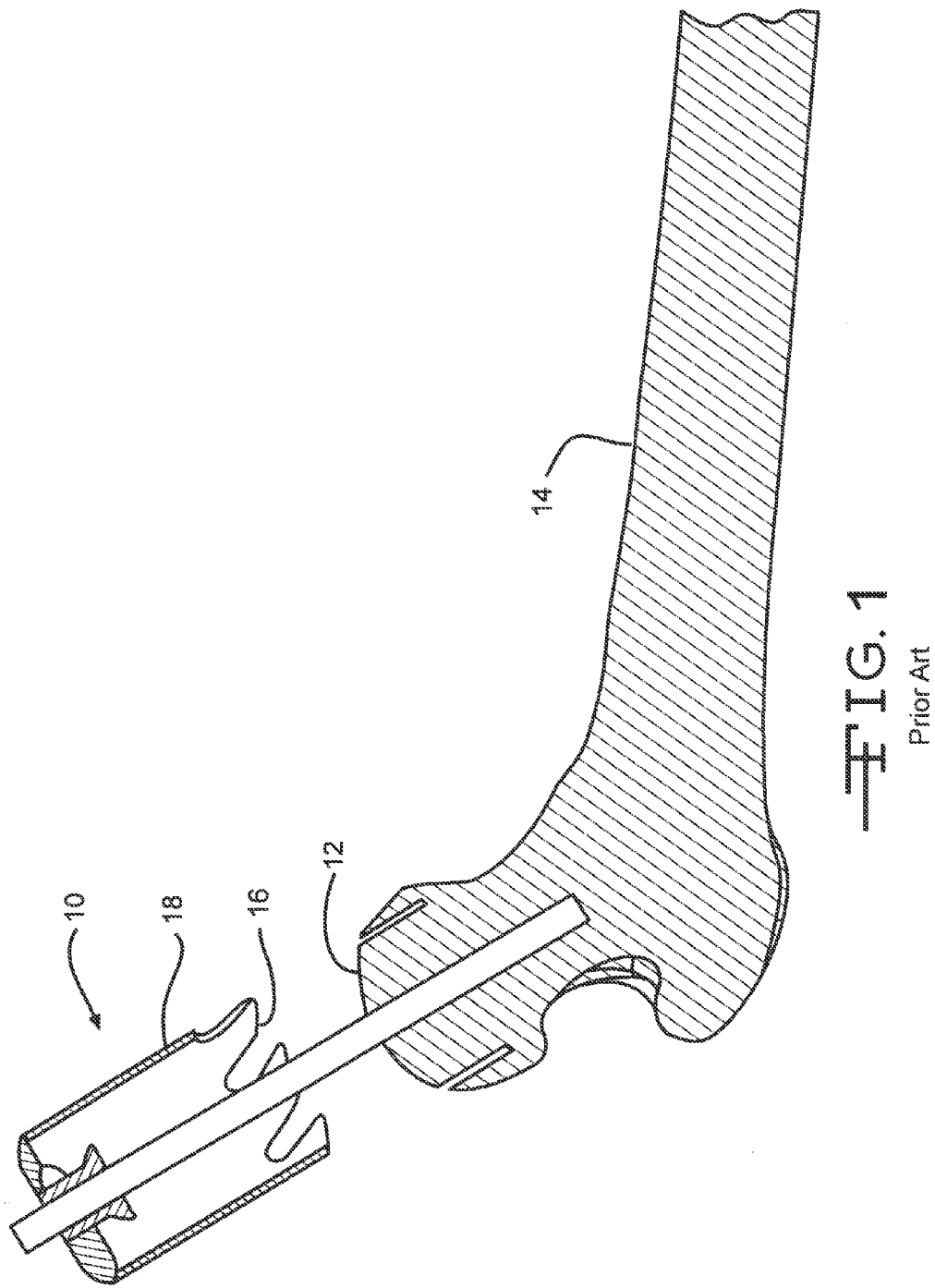
FIG. 1 is a cross-sectional view of the prior art bone cutter and bone.
Figure 2:
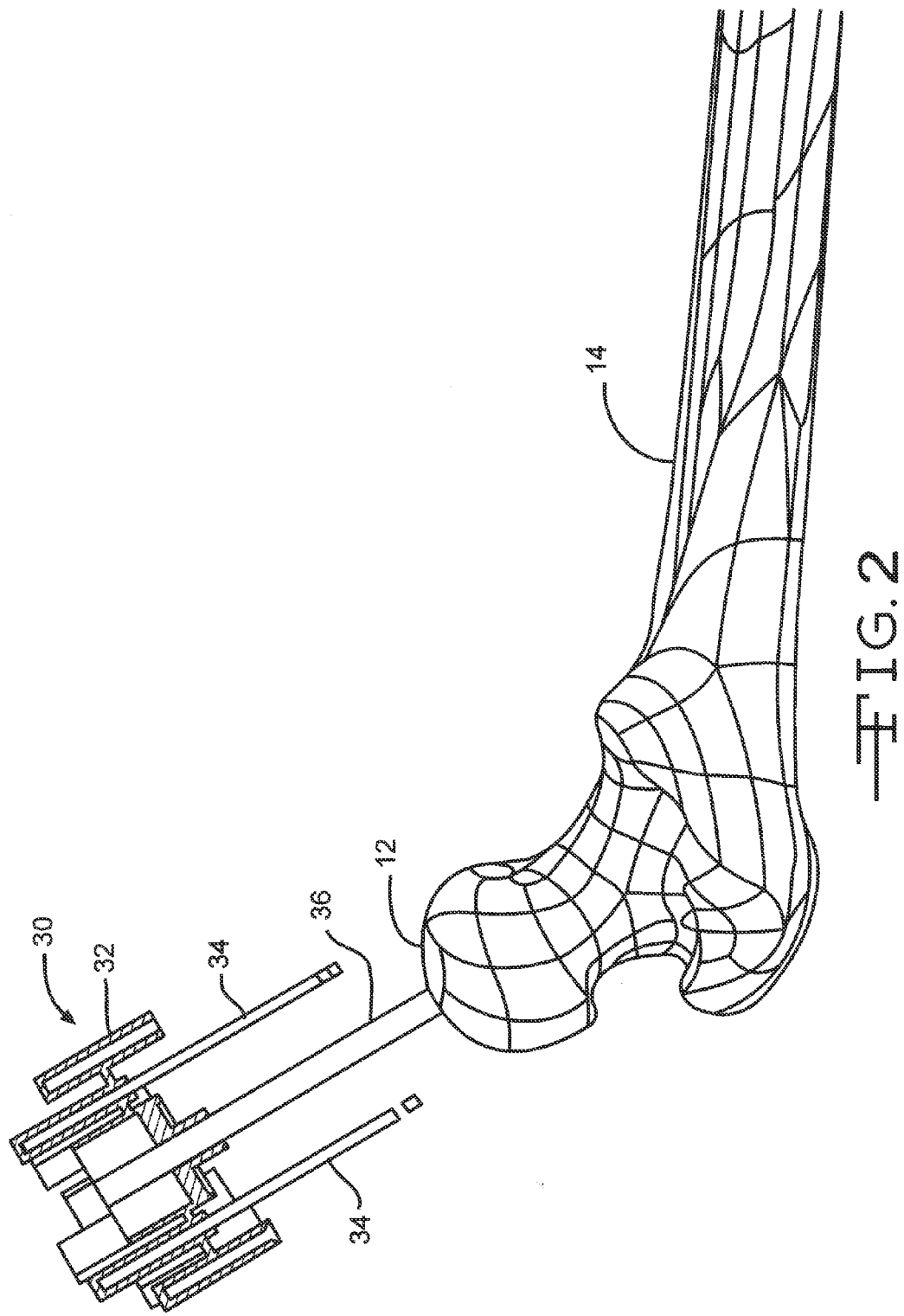
FIG. 2 is a perspective view of the bone cutter and guide-rod of the present invention.

Now turning to the figures, FIGS. 2-10 illustrate embodiments of the disposable bone cutter 30 of the present invention. As illustrated in FIG. 2, the bone cutter 30 comprises a cutter housing assembly 32, a plurality of insert blades 34 and a guide rod 36. As shown in FIGS. 3, 4, 5A, 6, 7 and 8, the cutter housing assembly 32 further comprises a plate 38, having a planar top surface 40, a planar bottom surface 42, a plate thickness 44 therebetween and a central longitudinal axis A-A therethrough.

As illustrated in FIGS. 3, 4, 5A, 6, and 8A the plate 38 preferably has a curved edge 46. More preferably, the plate 38 is generally of a spiral form. It is contemplated however, that the general shape of the plate 38 is non-limiting and may be of a rectangular, square, circular, oval, or triangular shape.

Figure 3:
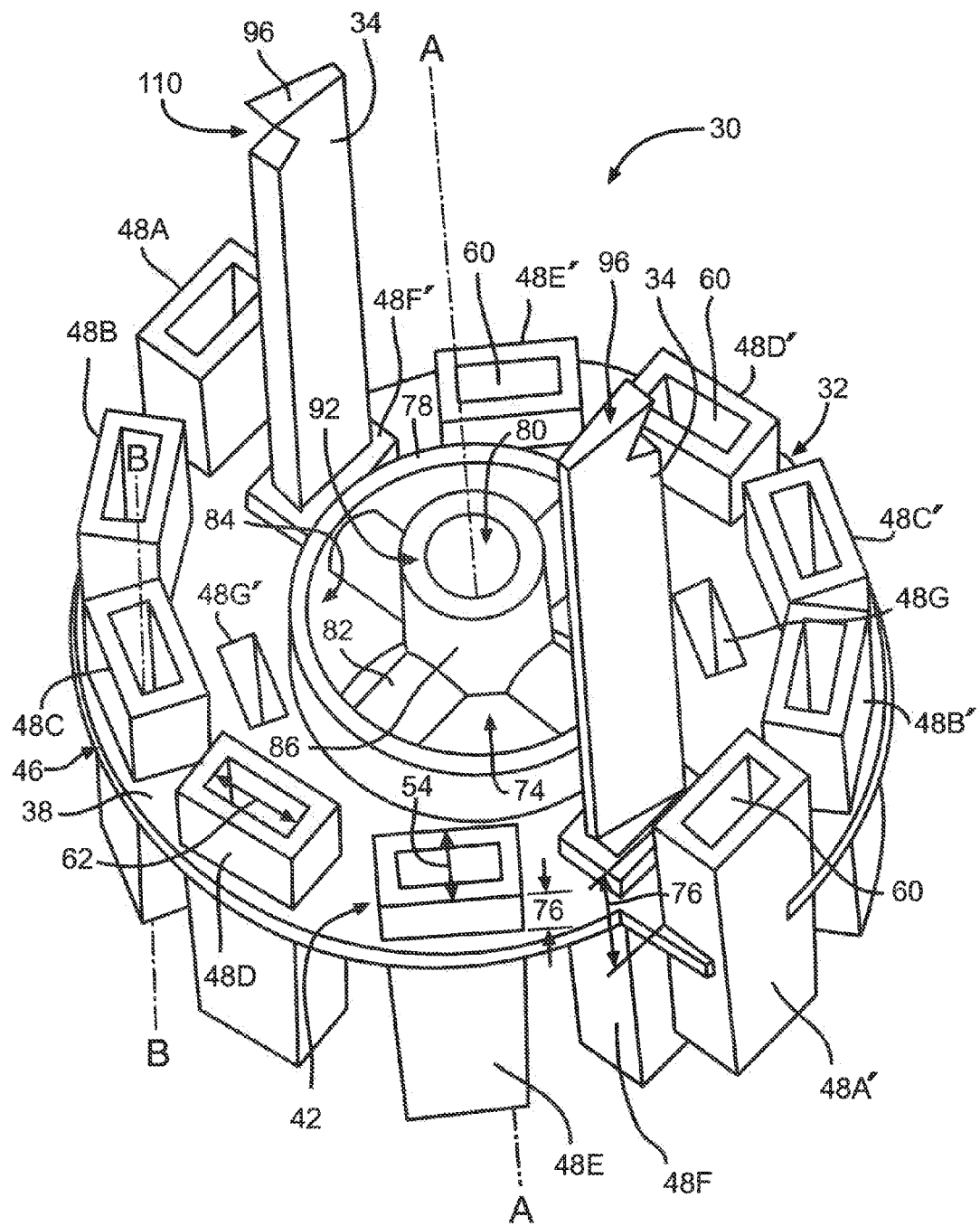
FIG. 3 is a perspective view of an embodiment of the bone cutter of the present invention taken from the distal end.
Figure 4:
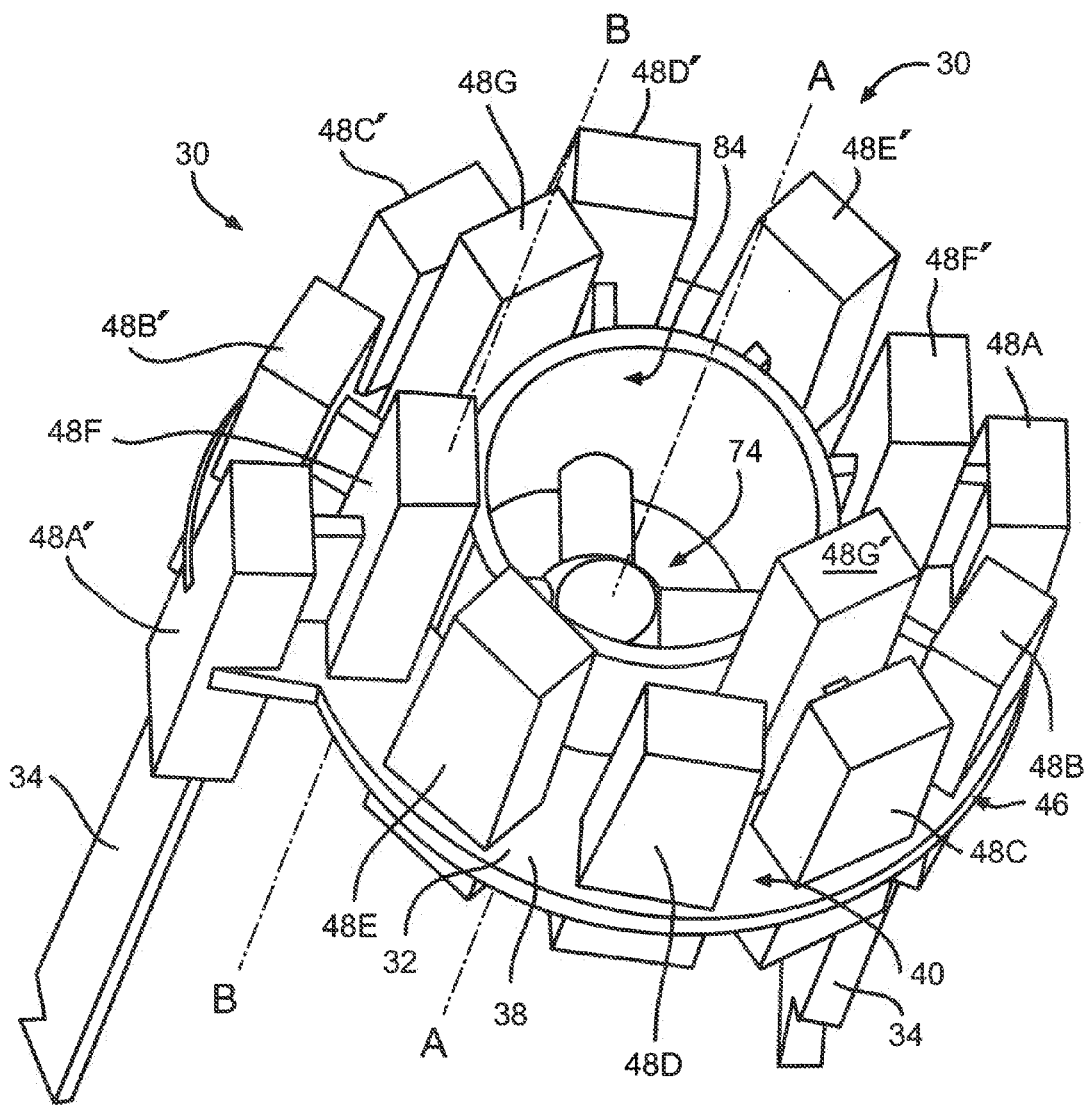
FIG. 4 is a perspective view of an embodiment of the bone cutter of the present invention taken from the perspective end.

A plurality of blade enclosures 48 is positioned through the thickness 44 of the plate 38 such that the central axis A-A is parallel to a blade enclosure longitudinal axis B-B as shown in FIGS. 3 and 4. It should be noted that although longitudinal axis B-B is illustrated through different examples of the plurality of blade enclosures 48 in FIGS. 3 and 4, each of the plurality of blade enclosures 48 has a longitudinal axis B-B that is parallel to central axis A-A.

In addition, each enclosure 48 has an enclosure width 50, an enclosure length 52, and an enclosure depth 54 that extends along enclosure longitudinal axis B-B. Furthermore, each blade enclosure 48 comprises a proximal end region 56 and a distal end region 58.

In a preferred embodiment, the width 50 of the blade enclosure 48 ranges from about 5 mm to about 20 mm, the length 52 of the blade enclosure 48 ranges from about 10 mm to about 50 mm and the depth 54 of the blade enclosure 48 ranges from about 2 mm to about 10 mm.

As illustrated in FIGS. 3, 5A, 6, and 8A, each enclosure 48 further comprises an opening 60 therewithin. This opening 60 allows for the insertion of the insert blade 34. Each blade enclosure opening 60 comprises an opening width 62, an opening length 64 and an opening depth 66 that extends from the distal end 72 of the blade enclosure 48 to a position within the proximal end region 70 thereof. An enclosure wall with a wall thickness ranging from about 0.5 mm to about 5 mm, surrounds the opening 60 of the enclosure 48. In a preferred embodiment, the opening width 62 ranges from about 2 mm to about 20 mm, the opening length 64 ranges from about 10 mm to about 45 mm and the opening depth 66 ranges from about 0.5 mm to about 5 mm.

As illustrated in FIG. 4, it is preferred that the proximal end 56 of the blade enclosure 48 is closed. However, it is contemplated that the proximal end 70 of the blade enclosure 48 may have an opening, thereby creating a throughbore (not shown) that extends through both the proximal and distal ends 70, 68 of the blade enclosure 48.

In a preferred embodiment, the opening 60 of the blade enclosure 48 is tapered. More specifically, the width 62 of the opening 60 of the blade enclosure 48 at the distal end 58 is greater than at the proximal end 56. This preferred tapered opening 60 embodiment is designed to provide the insert blade 34 with a snug fit. In an alternate embodiment, the blade enclosure 48 is tapered such that its width at the distal end 68 is greater than at the proximal end 70.

In a preferred embodiment, the plurality of blade enclosures 48 are aligned such that the distal end region 58 of each of the blade enclosures 48 is directed towards the distal end region 72 of the housing assembly 48. Furthermore, each of the individual blade enclosures 48 is positioned such that their longitudinal axes B-B are parallel to the central longitudinal axis A-A of the housing assembly 32.

In a preferred embodiment of the present invention, the plurality of the blade enclosures 48 are arranged in a spiral orientation about a central through bore 74 of the housing assembly 32, as shown in FIGS. 4, 5A, 6 and 8A. Furthermore, it is preferred that for each of the plurality of blade enclosures 48, there is a corresponding blade enclosure 48 positioned directly across and equidistant from the central longitudinal axis A-A of the assembly 32. In other words, the central longitudinal axis A-A of the housing assembly 32 is similar to that of a "mirror plane" in that there are "paired" blade enclosures 48. As shown in FIGS. 3, 5A, 6 and 8A, these "paired" blade enclosures 48 are designated as 48A and A', 48B and B', 48O and C', 48D and D', 48E and E', 48F and F', 48G and G'. The enclosures 48 pairs face each other with there being an equal distance between the central axis A-A and the blade enclosure longitudinal axis B-B of each of the "paired" blade enclosures 48. For example, the distance between the central axis A-A and 48A is equal to the distance between the central axis A-A and the longitudinal axis B-B of A'. In a preferred embodiment, this distance can range from about 10 mm to about 40 mm.

Figure 6:
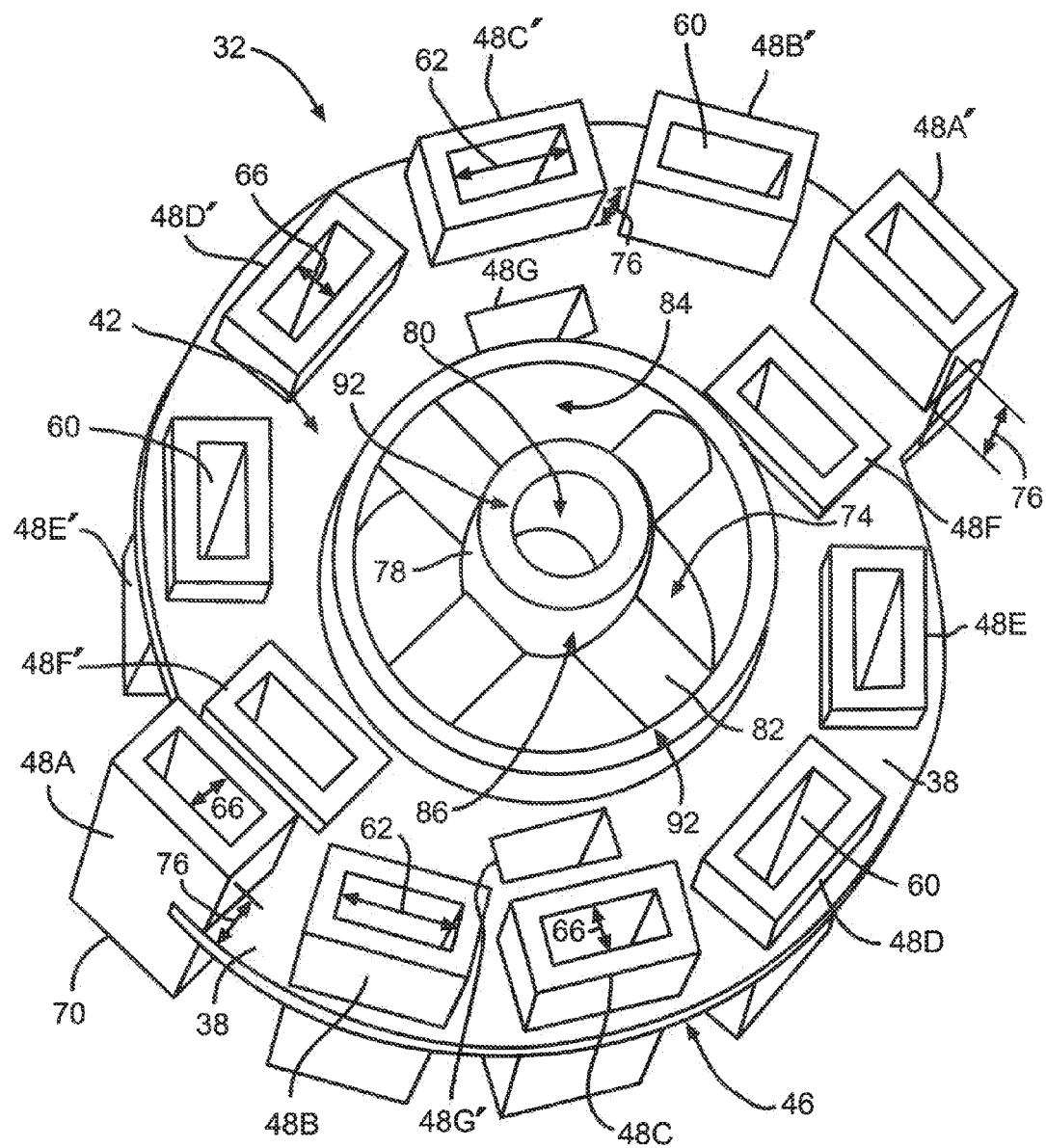
FIG. 6 is a perspective view of an embodiment of the cutter housing assembly of the present invention.
Figure 7:
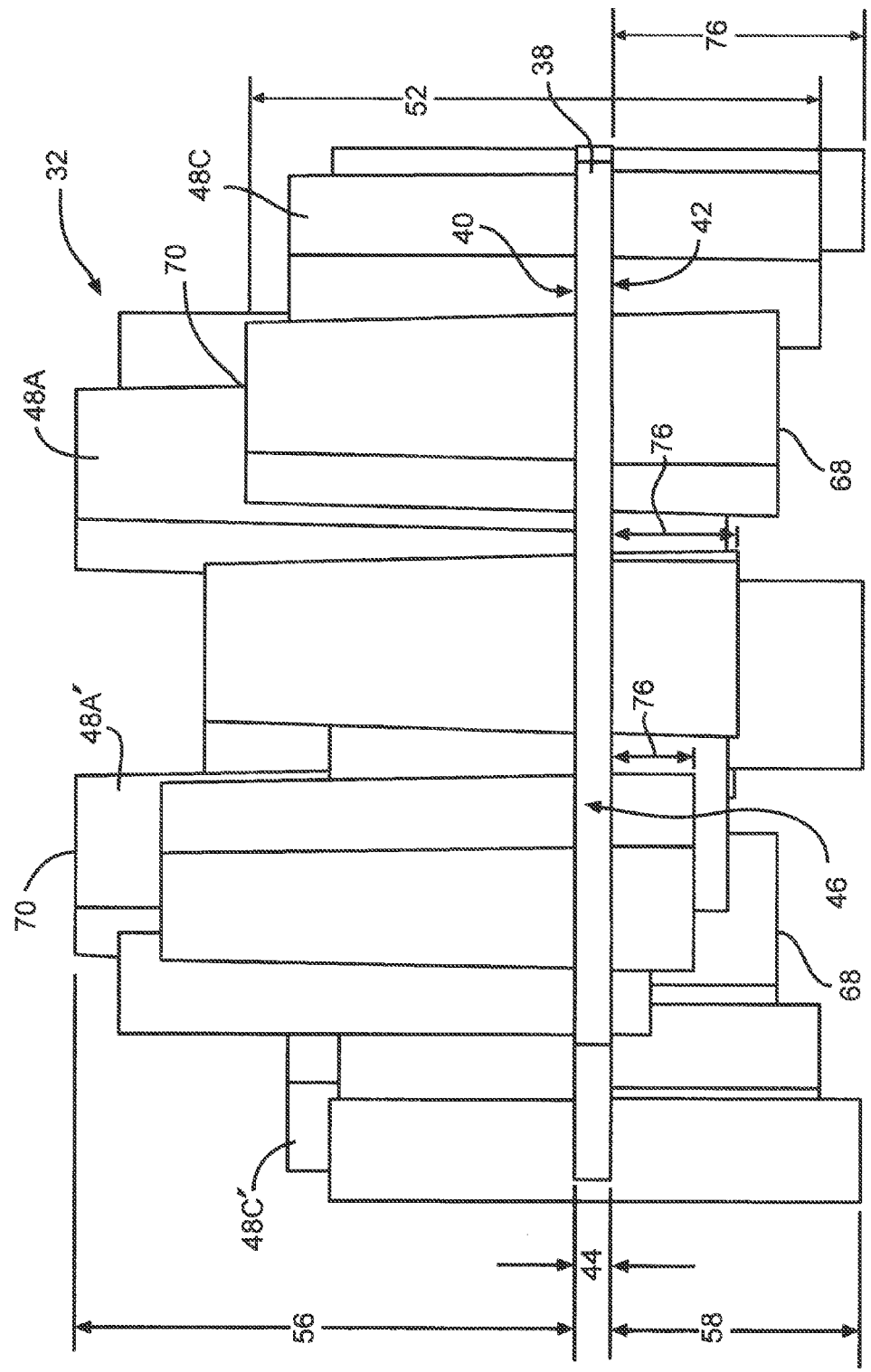
FIG. 7 is a side view illustrating the cutter housing assembly of the present invention.
Figure 8:
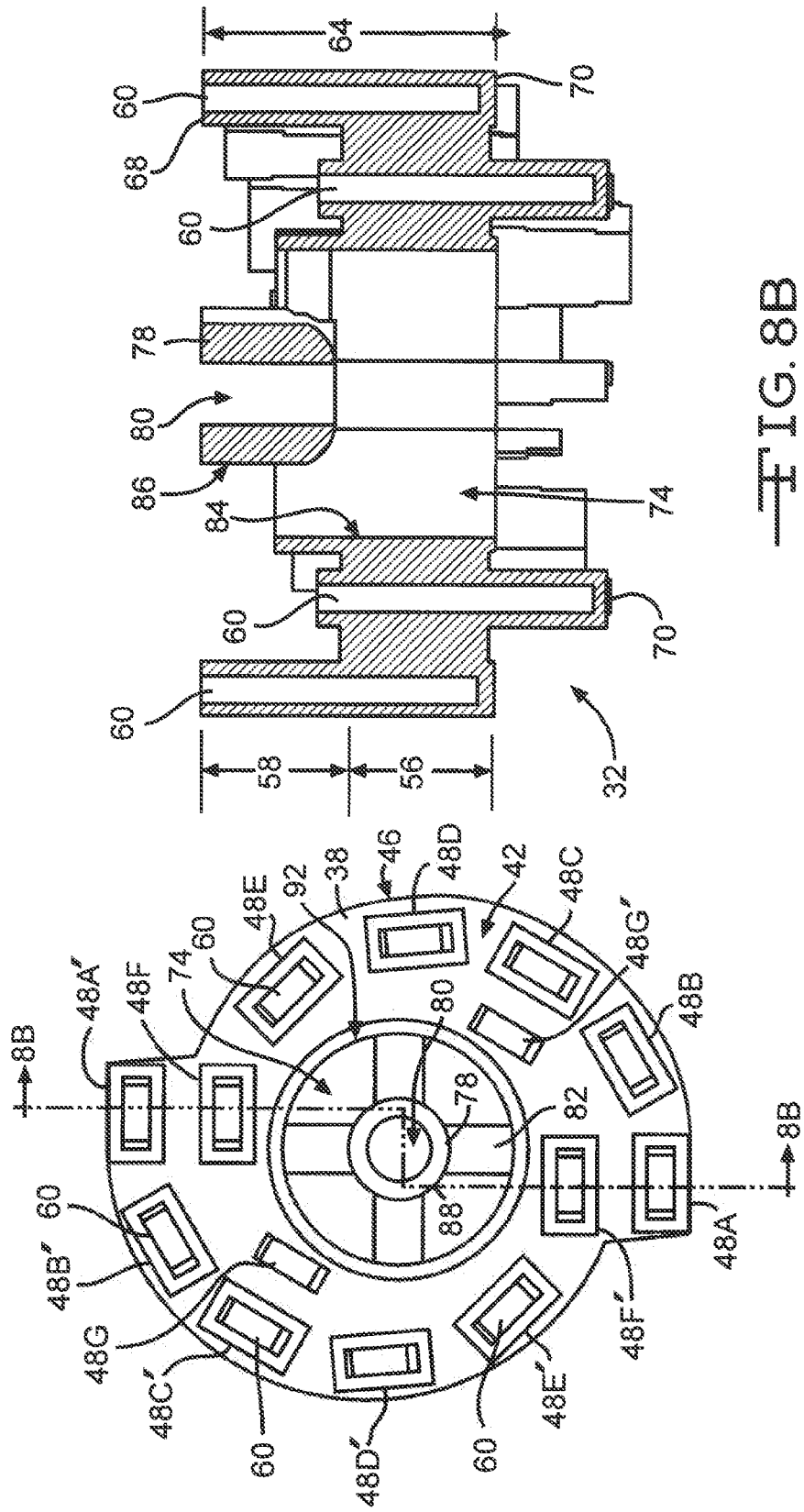
FIG. 8A is a bottom view illustrating a preferred embodiment of the housing assembly of the present invention.
FIG. 8B is a cross-sectional view of the housing assembly taken along cross-sectional line 8B-8B of FIG. 8A.

In addition, it is further preferred that the plurality of blade enclosures 48 are positioned at varying height intervals 76 below the bottom surface 42 of the plate 38. A height interval 76 is herein defined as the distance between the distal end 68 of the blade enclosure 48 and the bottom surface 42 of the plate 38, as shown in FIGS. 3, 6 and 7. In a preferred embodiment, the height interval 76 ranges from about 0 cm, i.e. flush with the bottom surface 42 of the plate 38, to about 20 mm. It is further preferred that each "paired" enclosure 48A/48A' to 48G/48G' (FIGS. 3 and 6), have a similar height interval 76.

In a preferred embodiment shown in FIGS. 3, 4, 5A, 6 and 8A, the housing assembly 32 has a boss 78 that is positioned within the central through-bore 74 of the assembly 32. More specifically, the boss 78 is centrally positioned within the through-bore 74 of the housing assembly 32 and is co-axial with the central longitudinal axis A-A. In a preferred embodiment, the boss 78 comprises a bore 80.

A plurality of bars 82, secure the boss 78 within the central through-bore 74 of the assembly 32. The bars 82 have a length 88 from about 5 mm to about 30 mm and a thickness 90 from about 5 mm to about 10 mm, and fluidly extend from the interior wall surface 84 of the through-bore 74 of the assembly 32 to the exterior wall surface 86 of the boss 78. It is preferred that a plurality of at least two bars 82 connect the boss 78 within the through-bore 74 of the assembly 32. Although it is preferred that these bars 82 have a round cross-section, as illustrated in FIGS. 3, 4, 5A, 6, and 8A, they may be designed with a multitude of non-limiting cross-section shapes such as rectangular, square, triangular and the like.

In a preferred embodiment, illustrated in FIGS. 3 and 6, the boss 78 is constructed with a distal planar edge 92. This distal planar edge 92 is designed to act as a "stop" to prevent further advancement of the cutter 30 into the end 12 of the bone 14. The boss 78 is preferably positioned within the central through-bore 74 of the plate 38 such that a cut depth 94, defined between the distal planar edge 92 of the boss 78 and the distal end surface 96 of the insert blade 34 is created. It is contemplated that this distal planar edge 92 can be positioned anywhere within the central through-bore 74 of the plate 38 to establish an optimal cut depth 94 for a particular implant (not shown). In a preferred embodiment, the cut depth 94 ranges from about 20 mm to about 100 mm.

It is preferred that the housing assembly 32 be composed of a biocompatible material. In a preferred embodiment, the assembly 32 is composed of a biocompatible thermoplastic such as, but not limited to, Acrylonitrile Butadiene Styrene (ABS), Polyarylamide (PAA), or Polyetheretherketone (PEEK).

Figure 9:
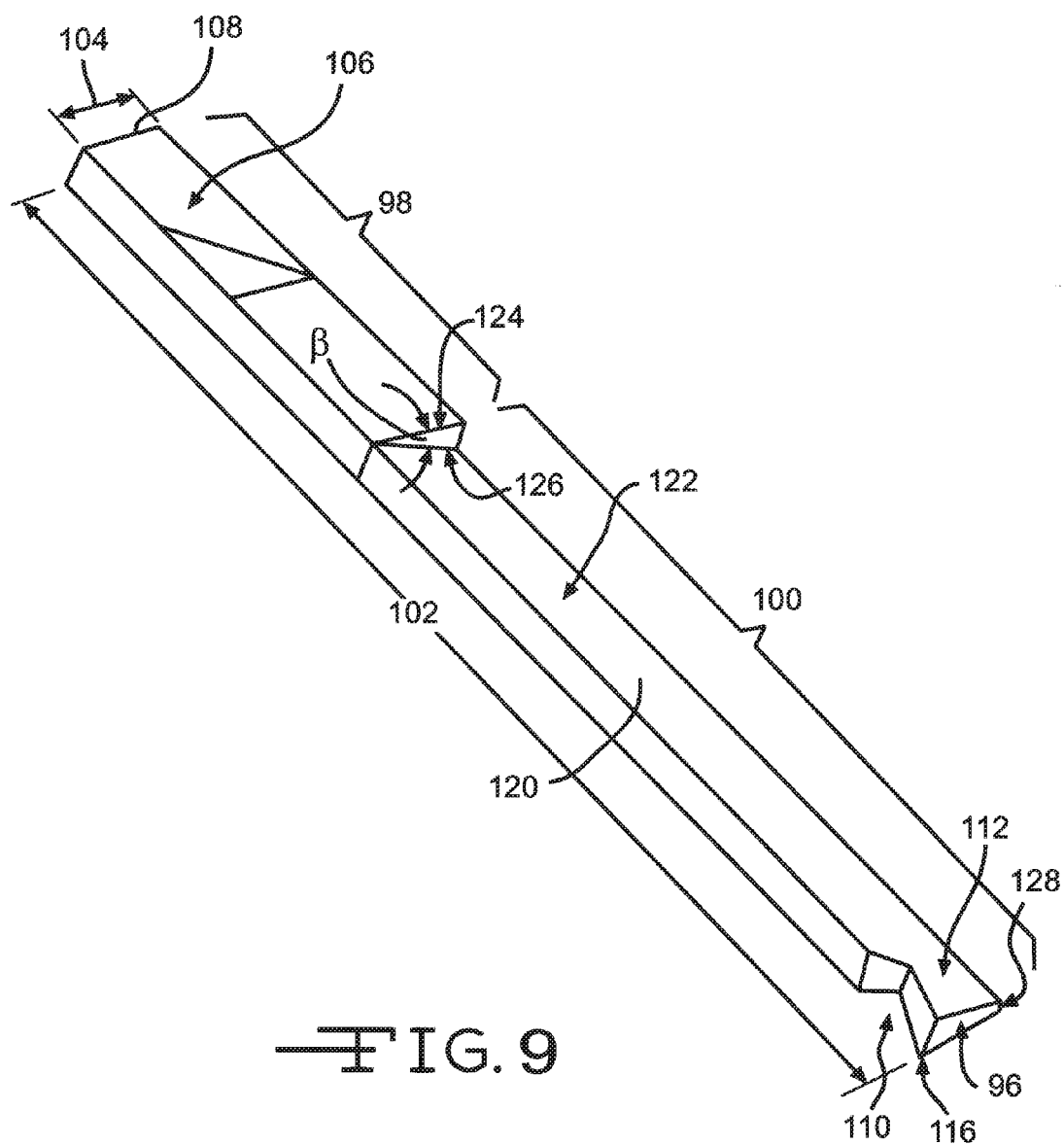
FIG. 9 is a perspective view of an embodiment of the insert blade of the present invention.
Figure 10:
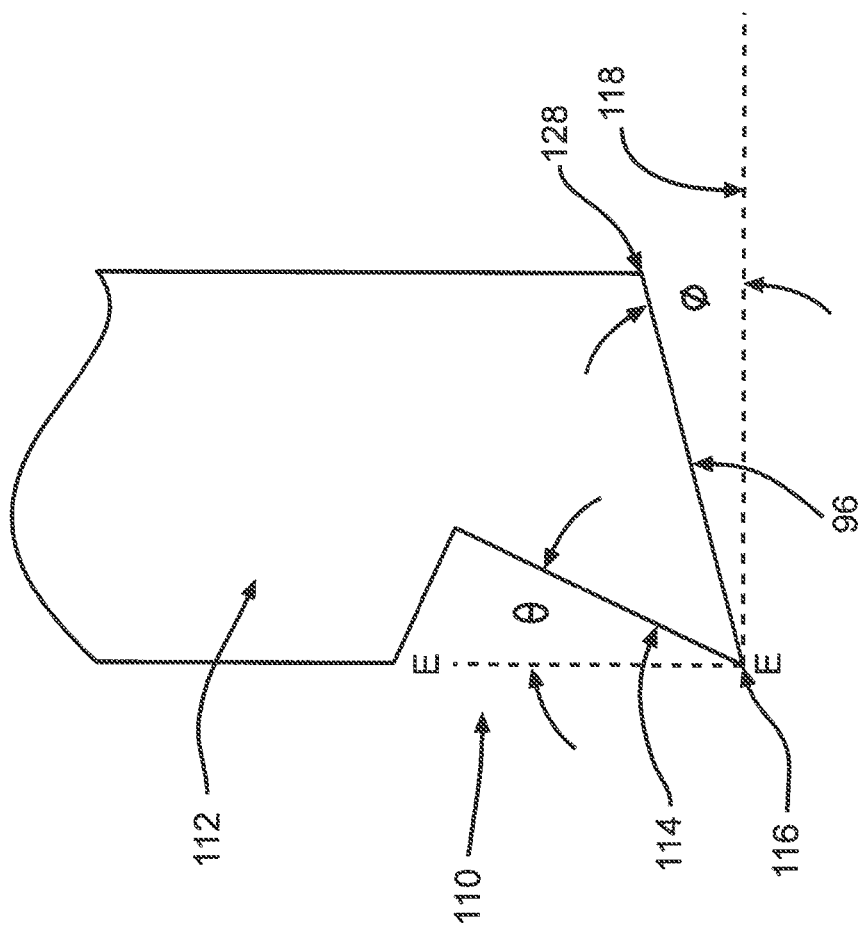
FIG. 10 is a magnified side view of the distal end region of the insert blade of the present invention shown in FIG. 9.

FIGS. 9 and 10 illustrate preferred embodiments of the insert blade 34 of the present invention. The insert blade 34 is preferably made from a biocompatible metal such as stainless steel, MP35N, titanium, and combinations thereof. Each insert blade 34 comprises a proximal blade region 98, a distal blade region 100 and a blade length 102 therebetween.

In a preferred embodiment, the proximal blade region 98 comprises a tapered proximal end blade width 104 with a roughened surface 106. The proximal end 98 of the blade 34 is designed and dimensioned to be inserted into the blade enclosure 48. The roughened surface 106 provides for an interference fit within the blade enclosure 48.

As illustrated in FIGS. 9 and 10, a groove 110 is preferably formed within the surface 112 of the distal end region 100 of the insert blade 34. In a preferred embodiment, the groove 110 has a "V" shape. The groove 110 is designed to establish a rake angle θ of the insert blade 34. The rake angle θ is defined as the intersection between the distal surface 114 of the groove 110 and a line E-E perpendicular to the cutting edge surface 116, as shown in FIG. 10. It is preferred that rake angle θ range from about 4° to about 30°.

A relief angle Ø, as illustrated in FIG. 10, is formed between the intersection of the distal end surface 96 of the blade 34 and a cut surface 118. The cut surface 118 is herein defined as the surface 118 that is cut by the cutter 30 of the present invention, such as the surface of a femur bone 14. It is preferred that the relief angle Ø range from about 4° to about 20°.

In a preferred embodiment, the distal region 100 of the insert blade 34 has a chamfered portion 120. More specifically, the chamfered portion 120 of the insert blade 34 is characterized by a region of the blade 34 that has been removed as illustrated in FIGS. 9 and 10. In a more preferred embodiment, the chamfered portion 120 has a chamfer angle β that ranges from about 5° to about 45°. The chamfer angle β is measured between the distal edge 124 of the proximal region 98 of the insert blade 34 and the proximal edge 126 of the chamfer portion 120, as shown in FIG. 9. The chamfer portion 120 is designed such that the cutting edge 116 of the blade 34 is wider than the trailing edge 128 of the blade 34. The chamfered portion 120 ensures that the trailing edge 128 does not interfere with the cut of the blade 34 as it is rotated about the end 12 of the bone 14.

In a preferred embodiment, each of the insert blades 34 are secured in the blade enclosure 48 via an induction bonding process. In this preferred embodiment, electromagnetic current heats the metal of the insert blade 34, thereby causing the polymeric body of the blade enclosure 48 to melt, solidifying a bond between the blade 34 and enclosure 48. In an equally preferred embodiment, a snap fit engagement of the insert blade 34 and blade enclosure 48 may also be designed. It is also contemplated that adhesives, cross pinned engagements, direct insert molding or ultrasonic insertion may also be used to secure and/or strengthen the bonding of the blade 34 within the enclosure 48.

Now, it is therefore apparent that the present invention has many features and benefits among which are promoting proper implant fit, decreased procedural times and minimized patient trauma. While embodiments of the present invention have been described in detail, that is for the purpose of illustration, not limitation.

What is claimed is:

1. A bone cutter comprising:
   a) a plate having a top surface extending to a bottom surface with a thickness therebetween, wherein a first longitudinal axis is aligned substantially perpendicular to at least one of the top and bottom plate surfaces;
   b) at least two blade enclosures supported by the plate, each enclosure comprising:
      i) an enclosure sidewall extending along a second longitudinal axis from an enclosure proximal portion to an enclosure distal end, wherein a first distal end of a first blade enclosure is either flush or protrudes below the plate bottom surface a first distance and a second distal end of a second blade enclosure protrudes below the plate bottom surface a second distance greater than the flush or first distance of the first enclosure; and
      ii) a blade enclosure opening extending along the enclosure sidewall to an enclosure distal open end,
      iii) wherein the second longitudinal axes of the at least two blade enclosures are substantially parallel to each other and spaced from, but substantially parallel toe the first longitudinal axis of the plate; and
   c) at least two insert blades, each blade having a blade proximal region extending to a distal cutting surface, wherein each of the at least two blades are positionable within a respective blade enclosure so that the blade proximal region resides within the blade enclosure opening and the distal cutting surface extends outwardly from the enclosure distal open end.

2. The bone cutter of claim 1 wherein the plate is of a general shape selected from the group consisting of a spiral, a circle, a rectangle, an oval, a triangle, and a square.

3. The bone cutter of claim 1 wherein at least three blade enclosures are supported by the plate in a spiral pattern about the first longitudinal axis.

4. The bone cutter of claim 3 wherein a first radial distance from the second longitudinal axis of a first enclosure to the first longitudinal axis is less than a second radial distance from the second longitudinal axis of a second enclosure to the first longitudinal axis, and wherein the second radial distance is less than a third radial distance from the second longitudinal axis of a third enclosure to the first longitudinal axis.

5. The bone cutter of claim 1 wherein the at least two blade enclosures are supported by the plate at equal radial distances from the first longitudinal axis.

6. The bone cutter of claim 1 wherein the at least two blade enclosures are diametrically opposite each other.

7. The bone cutter of claim 1 wherein a central through-bore extends through the thickness of the plate co-axial with the first longitudinal axis.

8. The bone cutter of claim 7 wherein a boss, residing within the plate has a boss through-bore that is co-axial with the first longitudinal axis.

9. The bone cutter of claim 7 wherein the plate trough-bore is configured to receive a guide rod.

10. The bone cutter of claim wherein each of the least two blades comprises a chamfered portion.

11. The bone cutter of claim 1 wherein the plate and the at least two blade enclosures are of a biocompatible material.

12. The bone cutter of claim 1 wherein a groove extends into a thickness of the insert blade at the distal cutting surface.

13. The bone cutter of claim l wherein a relief angle is formed in the blade at the distal cutting surface.

14. The bone cutter of claim 1 wherein a first plurality of blade enclosures are supported by the plate in a first spiral pattern and a second plurality of blade enclosures are supported by the plate in a second spiral pattern, and wherein the first and second pluralities of enclosures spiral outwardly in a clock-wise direction with respect to a view looking along the first longitudinal axis and toward the bottom plate surface.

15. The bone cutter of claim 1 wherein the at least two blades are of the same length and the respective blade enclosure openings of the at least two blade enclosures are of the same length so that a first cutting surface of the first blade is closer to the bottom plate surface than a second cutting surface of the second blade.

16. The bone cutter of claim 1 wherein the blade enclosure opening is tapered as the opening extends along the enclosure sidewall to the distal open end thereof.

17. A bone cutter comprising:
   a) a plate, having a top surface, a bottom surface with a thickness therebetween,wherein a first longitudinal axis is aligned substantially perpendicular to at least one of the top and bottom plate surfaces;

b) a plurality of blade enclosures supported by the plate, each blade enclosure comprising:
   i) an enclosure sidewall extending along a second longitudinal axis from an enclosure proximal portion to an enclosure distal end;
   ii) a blade enclosure opening extending along the enclosure sidewall to an enclosure distal open end,
   iii) wherein each of the plurality of blade enclosures are at least partially positioned through the thickness of the plate so that a portion of the blade enclosure protrudes below the bottom surface of the plate, and
   iv) wherein the second longitudinal axes of the plurality of blade enclosures are substanitially parallel to each other and spaced from, but substantially parallel to the first longitudinal axis of the plate; and
c) a plurality of insert blades, each blade having a blade proximal region extending to a distal cutting surface, wherein each of the plurality of blades are positionable proximal region resides within the blade enclosure opening and the distal cutting surface extends outwardly from the enclosure distal open end.

18. The bone cutter of claim 17 wherein the plate is of a general shape selected from the group consisting of a circle, a rectangle, an oval, a triangle, and a square.

19. The bone cutter of claim 17 wherein at least two of the plurality of blade enclosures are supported by the plate so that a portion of the enclosure protrudes above the top surface of the plate.

20. The bone cutter of claim 17 wherein at least two of the plurality of blade enclosures are supported by the plate so that a proximal end of the enclosure is about flush with the plate top surface 21. The bone cutter of claim 17 wherein at least three of the plurality of blade enclosure are supported by the plate in a spiral pattern about the first longitudinal axis.

22. The bone cutter of claim 21 wherein a first radial distance from the second longitudinal axis of a first enclosure to the first longitudinal axis is less than a second radial distance from the second longitudinal axis of a second enclosure to the first longitudinal axis, and wherein the second radial distance is less than a third radial distance from the second longitudinal axis of a third enclosure to the first longitudinal axis.

23. The bone cutter of claim 17 wherein a plate through-bore extending through the plate thickness is co-axial with the first longitudinal axis.

24. The bone cutter of claim 23 wherein a boss, having a boss residing within the plate has a boss through-bore that is coaxial with the first longitudinal axis.

25. The bone cutter of claim 23 wherein the plate through-bore is configured to receive a guide rod.

26. The bone cutter of claim 17 wherein each of the plurality of blades comprises a chamfer portion.

27. The bone cutter of claim 17 wherein the plate and the plurality of blade enclosures are of a biocompatible material.

28. The bone cutter of claim 17 wherein the blade enclosure opening is tapered as the opening extends along the enclosure sidewall to the distal open end thereof.

29. A bone cutter, comprising:
a) a plate having a top surface extending to a bottom surface with a thickness therebetween, wherein a first longitudinal axis extends perpendicular to the plate thickness;
b) a plurality of blade enclosures supported by the plate, each blade enclosure comprising an enclosure sidewall defining an enclosure opening extending along a second longitudinal axis to an enclosure distal open end, wherein the plurality of blade enclosures comprise:
   i) a first pair of blade enclosures that is supported by the plate diametrically opposed to each other, wherein the second axes of the first pair of blade enclosures are at a first radial distance from the first longitudinal axis, and wherein a first enclosure height extends from the bottom plate surface to the respective distal open ends of the first pair of enclosures;
   ii) a second pair of blade enclosures that is supported by the plate diametrically opposed to each other and spaced from the first pair of blade enclosures, wherein the second axes of the second pair of blade enclosures are at a second radial distance from the first longitudinal axis, and
   iii) wherein a second enclosure height extending from the bottom plate surface to the respective distal open ends of the second pair of enclosures is greater than the first enclosure height; and
c) a plurality of insert blades, each blade having a blade proximal region extending to a distal cutting surface, and wherein each of the blades are positionable within a respective enclosure so that a portion of the blade proximal region resides within the blade enclosure opening and the distal cutting end extends outwardly from the enclosure distal open end.

30. The bone cutter of claim 29 wherein a boss residing within the plate has a boss through-bore that is coaxial with the first longitudinal axis.

31. The bone cutter of claim 29 wherein the first or second enclosure heights range from 0 mm to about 20 mm.

32. The bone cutter of claim 29 wherein a first radial distance from the second longitudinal axis of a first enclosure to the first longitudinal axis is less than a second radial distance from the second longitudinal axis of a second enclosure to the first longitudinal axis.

33. The bone cutter of claim 29 wherein the blade enclosure opening is tapered as the opening extends along the enclosure sidewall to the distal open end thereof.

34. The bone cutter of claim 29 further comprising:
a) a third pair of blade enclosures that are supported by the plate diametrically opposed to each other and spaced from the second pair of enclosures, wherein the second axes of the third pair of enclosures are at a third radial distance from the first longitudinal axis, and wherein a third enclosure height extending from the bottom plate surface to the respective distal open ends of the third pair of enclosures is greater than the second enclosure height;
b) a fourth pair of blade enclosures that are supported by the plate diametrically opposed to each other and spaced from the third pair of enclosures, wherein the second axes of the fourth pair of enclosures are at a fourth radial distance from the first longitudinal axis, and wherein a fourth enclosure height extending from the bottom plate surface to the respective distal open ends of the fourth pair of enclosures is greater than the third enclosure height;
c) a fifth pair of blade enclosures that are supported by the plate diametrically opposed to each other and spaced from the fourth pair of enclosures, wherein the second axes of the fifth pair of enclosures are at a fifth radial distance from the first longitudinal axis, and wherein a fifth enclosure height extending from the bottom plate surface to the respective distal open ends of the fifth pair of enclosures is greater than the fourth enclosure height; and
d) a sixth pair of blade enclosures that are supported by the plate diametrically opposed to each other and spaced from the fifth pair of enclosures, wherein the second axes of the sixth pair of enclosures are at a sixth radial distance from the first longitudinal axis, and wherein a sixth enclosure height extending from the bottom plate surface to the respective distal open ends of the sixth pair of enclosures is greater than the fifth enclosure height.

35. The bone cutter of claim 34 wherein the first to sixth enclosure heights range from 0 mm to about 20 mm.

36. The bone cutter of claim 34 wherein a third radial distance from the second longitudinal axis of the third enclosure to the first longitudinal axis is greater than the second radial distance from the second longitudinal axis of the second enclosure to the first longitudinal axis, and wherein a fourth radial distance from the second longitudinal axis of the fourth enclosure to the first longitudinal axis is greater than the third radial distance from the second longitudinal axis of the third enclosure to the first longitudinal axis, wherein a fifth radial distance from the second longitudinal axis of the fifth enclosure to the first longitudinal axis is greater than the fourth radial distance from the second longitudinal axis of the fourth enclosure to the first longitudinal axis, and wherein a sixth radial distance from the second longitudinal axis of the sixth enclosure to the first longitudinal axis is greater than the fifth radial distance from the second longitudinal axis of the fifth enclosure to the first longitudinal axis.

37. The bone cutter of claim 36 wherein the first and sixth enclosures of each of the respective pairs are aligned along an imaginary plane.

* * * * *